United States Patent
Talley

[19]

[11] Patent Number: 6,058,935

[45] Date of Patent: May 9, 2000

[54] HEAD BELT

[76] Inventor: Mary Ann Talley, 1502 W. 92nd St., Los Angeles, Calif. 90047

[21] Appl. No.: 09/398,852

[22] Filed: Sep. 17, 1999

[51] Int. Cl.[7] .................................................. A61F 5/56
[52] U.S. Cl. .......................... 128/848; 128/857; 602/902; 606/204.15
[58] Field of Search .................................. 128/846, 848, 128/857, 858; 602/17, 902; 606/204.15, 204.35

[56] References Cited

U.S. PATENT DOCUMENTS

| | | | |
|---|---|---|---|
| D. 235,788 | 7/1975 | Eberhardt | D34/5 K |
| 2,711,730 | 6/1955 | Rogers | 128/848 |
| 4,189,141 | 2/1980 | Rooney | 272/95 |
| 4,207,881 | 6/1980 | Richter | 602/17 |
| 4,366,815 | 1/1983 | Broomes | 128/848 |
| 5,484,359 | 1/1996 | Wabafiyebazu | 248/11 |
| 5,687,743 | 11/1997 | Goodwin | 128/848 |
| 5,787,894 | 8/1998 | Holt | 128/848 |

*Primary Examiner*—Michael A. Brown
*Attorney, Agent, or Firm*—Goldstein & Canino

[57] ABSTRACT

A head belt including an elongated elastic band having short opposed end edges and long opposed side edges formed in a generally rectangular configuration. The short opposed end edges have corresponding male and female fasteners for securing the band around a head and under a chin of a wearer. The width and length of the elastic band can be adjusted to accommodate various users.

3 Claims, 2 Drawing Sheets

HEAD BELT

BACKGROUND OF THE INVENTION

The present invention relates to a head belt and more particularly pertains to preventing a person's chin from sagging while exercising.

In today's exercised crazed society, there is always a need to protect muscles and joints from injury. The existence of devices to protect knees, ankles, elbows, backs, shoulders, and other body parts are well known in the art. Most of these devices protect against injury for those participating in some type of rigorous activity, such as jogging. Jogging tends to create a large amount of pressure on the jogger's body. Most protective devices known in the art protect various parts of the jogger's body, but none has the primary purpose of protecting the jogger's face. While jogging, the jogger's face and, in particular, chin tends to sag downwardly. Continued jogging over long periods of time will subject the face to extreme sagging. What is needed is a protective device that can be worn over the head of a jogger that will prevent their chin and face from sagging.

The present invention attempts to solve the abovementioned problem by providing a device that is specifically designed for protecting the face and chin of the wearer during exercise.

The use of exercise devices is known in the prior art. More specifically, exercise devices heretofore devised and utilized for the purpose of exercising facial muscles are known to consist basically of familiar, expected and obvious structural configurations, notwithstanding the myriad of designs encompassed by the crowded prior art which have been developed for the fulfillment of countless objectives and requirements.

By way of example, U.S. Pat. No. 5,484,359 to Wabafiyebazu discloses a chin muscle toner comprised of an elastic strap secured over the forehead and under the chin. U.S. Pat. No. 4,189,141 to Rooney discloses a face mask to be worn while exercising various facial muscles. U.S. Pat. No. Des. 235,788 to Eberhardt discloses the ornamental design for a facial exerciser device.

While these devices fulfill their respective, particular objective and requirements, the aforementioned patents do not describe a head belt for preventing a person's chin from sagging while exercising.

In this respect, the head belt according to the present invention substantially departs from the conventional concepts and designs of the prior art, and in doing so provides an apparatus primarily developed for the purpose of preventing a person's chin from sagging while exercising.

Therefore, it can be appreciated that there exists a continuing need for a new and improved head belt which can be used for preventing a person's chin from sagging while exercising. In this regard, the present invention substantially fulfills this need.

SUMMARY OF THE INVENTION

In the view of the foregoing disadvantages inherent in the known types of exercise devices now present in the prior art, the present invention provides an improved head belt. As such, the general purpose of the present invention, which will be described subsequently in greater detail, is to provide a new and improved head belt and method which has all the advantages of the prior art and none of the disadvantages.

To attain this, the present invention essentially comprises an elongated elastic band having short opposed end edges and long opposed side edges formed in a generally rectangular configuration. The short opposed end edges have corresponding male and female fasteners for securing the band around a head and under a chin of a wearer. Width adjustment means are secured to the elongated band for adjusting a width of the elastic band. Length adjustment means are secured to the elongated band for adjusting a length of the elastic band.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved head belt which has all the advantages of the prior art exercise devices and none of the disadvantages.

It is another object of the present invention to provide a new and improved head belt which may be easily and efficiently manufactured and marketed.

It is a further object of the present invention to provide a new and improved head belt which is of durable and reliable construction.

An even further object of the present invention is to provide a new and improved head belt which is susceptible of a low cost of manufacture with regard to both materials and labor, and which accordingly is then susceptible of low prices of sale to the consuming public, thereby making such a head belt economically available to the buying public.

Even still another object of the present invention is to provide a new and improved head belt for preventing a person's chin from sagging while exercising.

Lastly, it is an object of the present invention to provide a new and improved head belt including an elongated elastic band having short opposed end edges and long opposed side edges formed in a generally rectangular configuration. The short opposed end edges have corresponding male and female fasteners for securing the band around a head and under a chin of a wearer. Width adjustment means are secured to the elongated band for adjusting a width of the elastic band. Length adjustment means are secured to the elongated band for adjusting a length of the elastic band.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various figures.

DESCRIPTION OF THE PREFERRED EMBODIMENT

Figure 1:
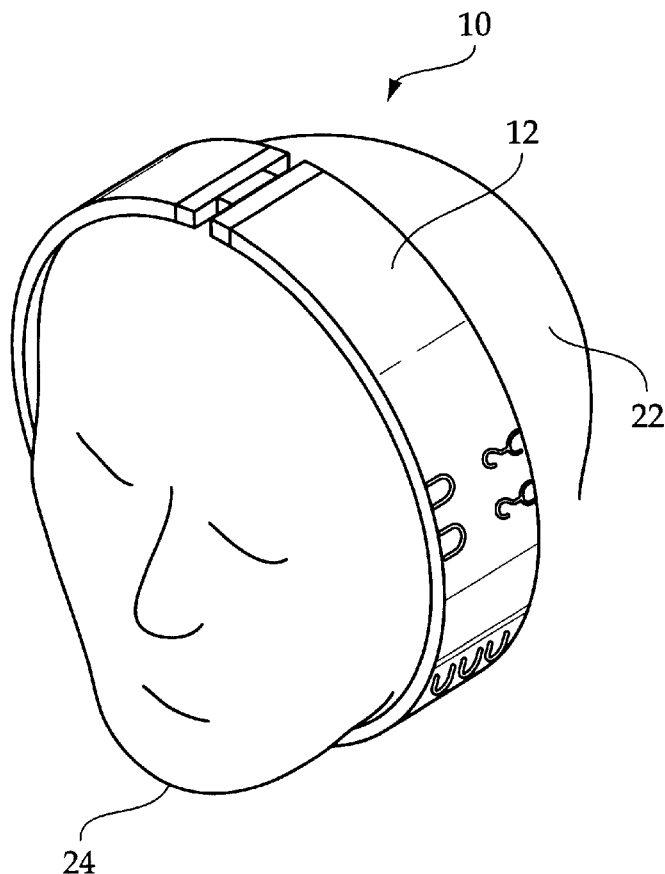
FIG. 1 is a perspective view of the preferred embodiment of the head belt constructed in accordance with the principles of the present invention.
Figure 2:
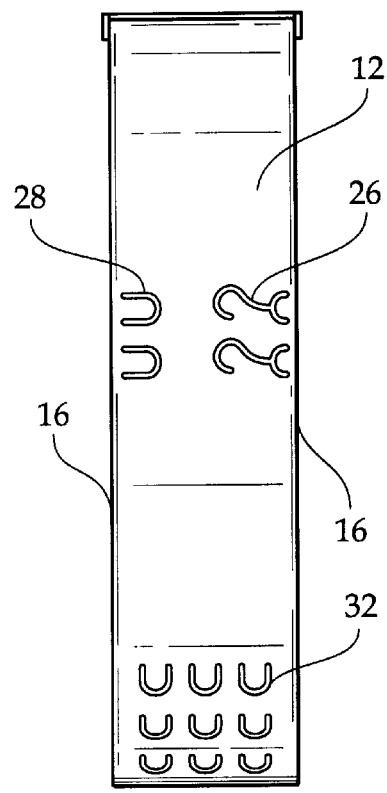
FIG. 2 is a plan view of the present invention.

With reference now to the drawings, and in particular, to FIGS. 1 through 4 thereof, the preferred embodiment of the new and improved head belt embodying the principles and concepts of the present invention and generally designated by the reference number 10 will be described.

Specifically, it will be noted in the various Figures that the device relates to a head belt for preventing a person's chin from sagging while exercising. In its broadest context, the device consists of an elongated elastic band, width adjustment means, and length adjustment means. Such components are individually configured and correlated with respect to each other so as to attain the desired objective.

The elongated elastic band 12 having short opposed end edges 14 and long opposed side edges 16 formed in a generally rectangular configuration. The short opposed end edges 14 have corresponding male and female fasteners 18,20 for securing the band 12 around a head 22 and under a chin 24 of a wearer.

Figure 3:
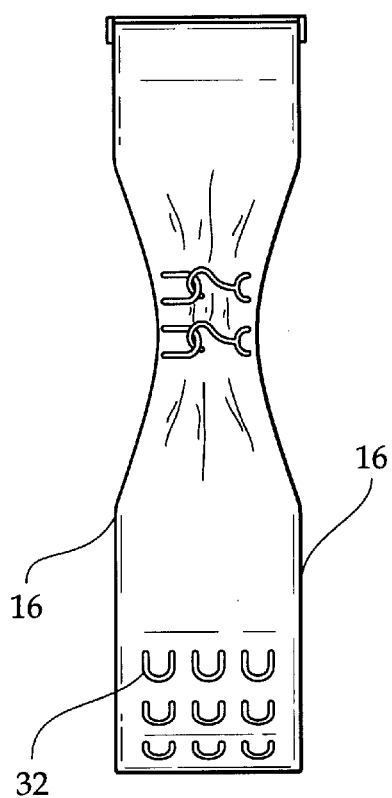
FIG. 3 is a plan view of the present invention illustrated in a narrowed orientation for user with small chins.
Figure 4:
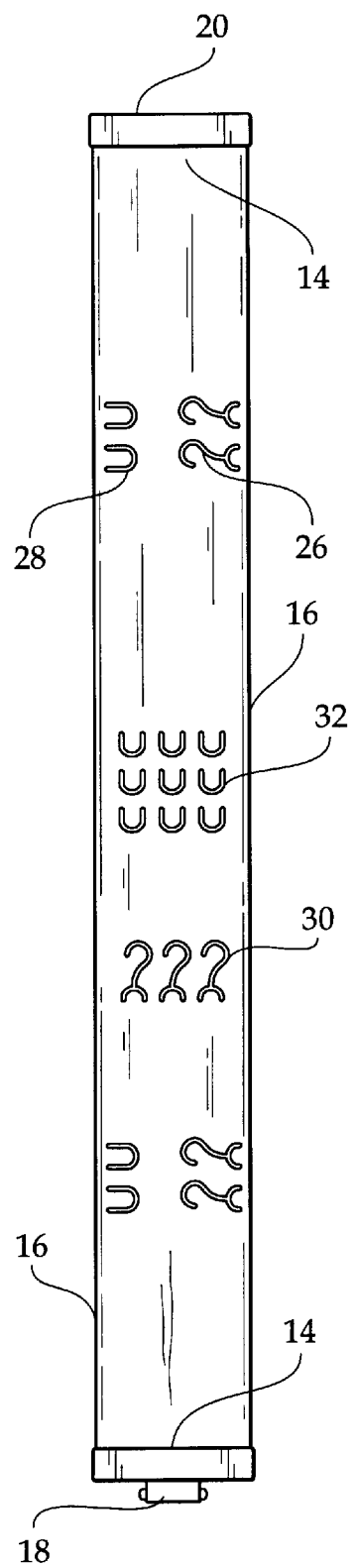
FIG. 4 is a plan view of the present invention illustrated in an extended orientation.

The width adjustment means are secured to the elongated band 12 for adjusting a width of the elastic band 12. The width adjustment means includes at least one pair of hooks 26 and corresponding loops 28 disposed inwardly of the long opposed side edges 16 of the elastic band 12. FIG. 3 illustrates the coupling of the hooks 26 and the loops 28 to narrow the width of the elastic band 12 so as to accommodate a user width a narrower chin.

The length adjustment means are secured to the elongated band 12 for adjusting a length of the elastic band 12. The length adjustment means includes a plurality of hooks 30 and corresponding loops 32 disposed centrally on the elastic band 12 inwardly of the opposed short end edges 14 and the opposed long end edges 16. The hooks 30 will be coupled with the loops 32 so as to shorten the length of the elastic band 12 so as to accommodate a person with a smaller head.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A head belt for preventing a person's chin from sagging while exercising comprising, in combination:

an elongated elastic band having short opposed end edges and long opposed side edges formed in a generally rectangular configuration, the short opposed end edges having corresponding male and female fasteners for securing the band around a head and under a chin of a wearer;

width adjustment means secured to the elongated band for adjusting a width of the elastic band;

length adjustment means secured to the elongated band for adjusting a length of the elastic band.

2. The head belt as set forth in claim 1 wherein the width adjustment means includes at least one pair of hooks and corresponding loops disposed inwardly of the long opposed side edges of the elastic band.

3. The head belt as set forth in claim 1 wherein the length adjustment means includes a plurality of hooks and corresponding loops disposed centrally on the elastic band inwardly of the opposed short end edges and the opposed long end edges.

* * * * *